(12) United States Patent
Li et al.

(10) Patent No.: US 9,483,441 B2
(45) Date of Patent: Nov. 1, 2016

(54) QUALITY CONTROL SYSTEM

(75) Inventors: Qing Li, Hitachinaka (JP); Masaharu Nishida, Hitachinaka (JP)

(73) Assignee: Hitachi High-Technologies Corporation, Tokyo (JP)

(*) Notice: Subject to any disclaimer, the term of this patent is extended or adjusted under 35 U.S.C. 154(b) by 827 days.

(21) Appl. No.: 13/809,956

(22) PCT Filed: Jun. 30, 2011

(86) PCT No.: PCT/JP2011/065023
§ 371 (c)(1),
(2), (4) Date: Feb. 21, 2013

(87) PCT Pub. No.: WO2012/011371
PCT Pub. Date: Jan. 26, 2012

(65) Prior Publication Data
US 2013/0151189 A1  Jun. 13, 2013

(30) Foreign Application Priority Data
Jul. 22, 2010  (JP) ................................ 2010-164446

(51) Int. Cl.
*G06F 17/00* (2006.01)
*G01N 35/00* (2006.01)

(52) U.S. Cl.
CPC ......... *G06F 17/00* (2013.01); *G01N 35/00712* (2013.01); *G01N 35/00613* (2013.01); *G01N 35/00693* (2013.01)

(58) Field of Classification Search
CPC ................ G01N 35/00613; G01N 35/00712; G01N 35/00693; G06F 17/00
See application file for complete search history.

(56) References Cited

U.S. PATENT DOCUMENTS

| 5,616,504 A * | 4/1997 | Brown ................... G01N 33/48 435/7.1 |
| 5,835,384 A * | 11/1998 | Lin ................... G01N 35/00594 700/9 |
| 6,579,717 B1 * | 6/2003 | Matsubara ....... G01N 35/00663 198/343.1 |

(Continued)

FOREIGN PATENT DOCUMENTS

| JP | 2007-248088 A | 9/2007 |
| JP | 2009-168730 A | 7/2009 |
| WO | 2010/073479 A1 | 7/2010 |

OTHER PUBLICATIONS

International Preliminary Report on Patentability received in International Application No. PCT/JP2011/065023 dated Feb. 21, 2013.

*Primary Examiner* — Shogo Sasaki
(74) *Attorney, Agent, or Firm* — Mattingly & Malur, PC

(57) ABSTRACT

In a clinical laboratory, the degree of contamination of an automatic analyzer may constantly change due, for instance, to the operation of the automatic analyzer and newly added examinations, and there is a risk of failure to adequately maintain the performance of the automatic analyzer by performing calibration at conventional intervals. Meanwhile, the result of quality control varies depending on the performance of an unsealed reagent. Hence, performing calibration at predetermined intervals may fail to flexibly calibrate the reagent when the performance of the reagent is changed by reagent replenishment or by contamination. Provided is a quality control method for issuing a warning to indicate an optimum calibration method and calibration intervals in accordance with the contents of a quality control screen and with the pattern of variation in the result of calibration.

3 Claims, 6 Drawing Sheets

(56) References Cited

U.S. PATENT DOCUMENTS

| | | | |
|---|---|---|---|
| 6,846,457 B1* | 1/2005 | Tokiwa | G01N 35/00594 422/63 |
| 7,925,461 B2* | 4/2011 | Yamaguchi | G06F 19/366 700/109 |
| 2004/0220761 A1* | 11/2004 | Yundt-Pacheco | G06F 19/366 702/84 |
| 2007/0217949 A1 | 9/2007 | Mimura et al. | |
| 2008/0114559 A1* | 5/2008 | Yamaguchi | G06F 19/366 702/84 |
| 2012/0000268 A1 | 1/2012 | Li et al. | |

* cited by examiner

QUALITY CONTROL SYSTEM

TECHNICAL FIELD

The present invention relates to a quality control system for a clinical examination automatic analyzer that mainly uses blood, urine, or other patient specimen for clinical examination, and more particularly to a quality control system that performs statistical processing on a quality control or calibration result obtained over a predetermined period of time and outputs an appropriate calibration method in accordance with the pattern and range of variation in the quality control or calibration result.

BACKGROUND ART

In quality control in an automatic analyzer at clinical examination, a quality control substance (control sample) is measured at predetermined time intervals during the measurements of patient specimens or measured whenever a predetermined number of specimens have been measured. A check is performed to determine whether the result of such quality control substance measurement is within a control range defined for the quality control substance. Alternatively, diurnal variation and day-to-day variation are studied to determine whether the degree of precision is within a control range. Further, the result of quality control substance measurement and the result of calibration performed at predetermined time intervals are used to determine whether the automatic analyzer is normal, whether a reagent is deteriorated or otherwise abnormal, and whether a standard solution is properly prepared.

The above-described quality control is exercised by having a clinical laboratory technician totalize, record, and store the results of calibration and quality control substance measurement.

A control value for a quality control substance is not only managed by a clinical laboratory technician in a clinical laboratory, but also managed by a public institution.

(1) The clinical laboratory manages the result of quality control substance measurement by using a commercially available quality control substance.

(2) The clinical laboratory sends data derived from its quality control substance measurement to a reagent manufacturer through a network or by mail or the like. The reagent manufacturer then performs statistical processing on the data and returns the result of processing to each hospital. The clinical laboratory manages the results of measurement and statistical processing.

(3) Japanese Society of Laboratory Medicine, Japan Medical Association, or other similar organization simultaneously distributes a common sample to hospitals, clinical laboratory centers, and other similar institutions in Japan several times a year and has them measure the common sample. The institutions totalize and perform statistical processing on the results of measurements. In addition, relevant surveys are conducted, for instance, on an individual prefecture basis or on an individual hospital group basis.

(4) An automatic analyzer manufacturer, which has sold and installed its automatic analyzer to various clinical laboratories in hospitals and to various laboratory centers, has established a practical remote monitoring system by connecting its service server to the automatic analyzer through a network.

A technology related to (4) above is described in Patent Document 1. A clinical laboratory in each hospital transmits, for example, a calibration result, a quality control substance measurement result, a reagent lot number and reagent bottle number used during measurement, a calibrator lot number/vial number, a quality control substance lot number/vial number, and alarm information in real time to a support center through a network. The support center totalizes and performs statistical processing on the calibration result and quality control substance data, and performs checks, for instance, to determine daily changes and the deviation from a reference value. The clinical laboratory accesses the support center through the network to confirm the quality control in an automatic analyzer.

PRIOR ART LITERATURE

Patent Document

Patent Document 1: JP-2007-248088-A

SUMMARY OF THE INVENTION

Problem to be Solved by the Invention

A primary object of the quality control system based on the above-described background art is to judge whether the result of quality control substance measurement is within the control range and judge whether variation in the result of quality control substance measurement is methodical or accidental.

If the result of quality control varies, the cause of such variation is analyzed, and calibration is performed. Subsequently, the quality control result derived from remeasurement is used to formulate a judgment.

However, the use of a conventional quality control system causes the following problems when quality control is exercised in accordance with the operation of a laboratory.

A first problem is that a patient specimen is usually measured after confirming the result of quality control by individually calibrating various items on a periodic basis. However, an operator unfamiliar with an automatic analyzer may merely check that the result of quality control measurement is within the control range, and measure the patient specimen without performing calibration.

Further, in some institutions calibration and quality control measurement are performed at predetermined intervals. If the calibration is simply performed at predetermined intervals, a reagent might not be adequately calibrated if reagent performance varies due to a reagent lot change.

In other words, if the method and frequency of the calibration are defined in accordance with rules unique to the laboratory, an unstable reagent may be inadequately calibrated to affect clinical results.

A second problem is that performing calibration at unnecessarily frequent intervals while the reagent is stable imposes an increased burden by causing, for instance, an increase in running cost and in man-hours.

Consequently, means of prompting for performing appropriate calibration at appropriate intervals is required in accordance with the automatic analyzer used in each clinical laboratory.

Means for Solving the Problem

The use of the following means solves the above problems.

Statistical processing is performed on the results of quality control and calibration of each reagent lot and of each reagent bottle. The results of statistical processing are accumulated. In accordance with variation in the result of quality control, statistical processing is performed on the absorbance of a reagent blank, the initial absorbance of the reagent blank, the difference between two measurements of standard solution absorbance, and a K factor. The degree of reagent deterioration and the result of quality control are determined from changes, for instance, in the absorbance of the reagent blank, in the initial absorbance of the reagent blank, or in the K factor to report the intervals at which the calibration should be performed and other details of the calibration.

The intervals at which the local institution should be calibrated are corrected for each reagent lot in accordance with the tendency of changes in the results of calibration at the other institutions. The corrected calibration intervals are then reported.

Advantageous Effects of the Invention

The following advantageous effects are provided when each hospital and the support center exercise quality control as described above.

Although the operations of a laboratory vary from one institution to another, its weekly operations tend to be repeated. Therefore, the pattern and range of variation in the previously obtained weekly results of a plurality of quality control substance measurements and calibration measurements can be extracted to determine the characteristics of the results of such weekly measurements.

If the characteristics of a plurality of previously obtained weekly measurement results indicate that the variation in the results of calibration measurements and quality control is insignificant, calibration intervals double the intervals of previous calibration can be reported as recommended calibration intervals. This makes it possible to adequately confirm the results of quality control and refrain from performing calibration at unduly short intervals.

If, on the other hand, the characteristics of the plurality of previously obtained weekly measurement results indicate that the variation in the results of calibration measurements and quality control is significant, calibration intervals one-half or one-third the intervals of previous calibration can be reported as recommended calibration intervals. This makes it possible to properly calibrate the reagent performance by performing calibration at optimum intervals.

Further, the necessity for additional calibration can be reported in accordance with the characteristics of variation in a reagent that is derived from the same lot and used in the other laboratories. This makes it possible to avoid the risk of potential quality control failure.

MODE FOR CARRYING OUT THE INVENTION

Figure 1:
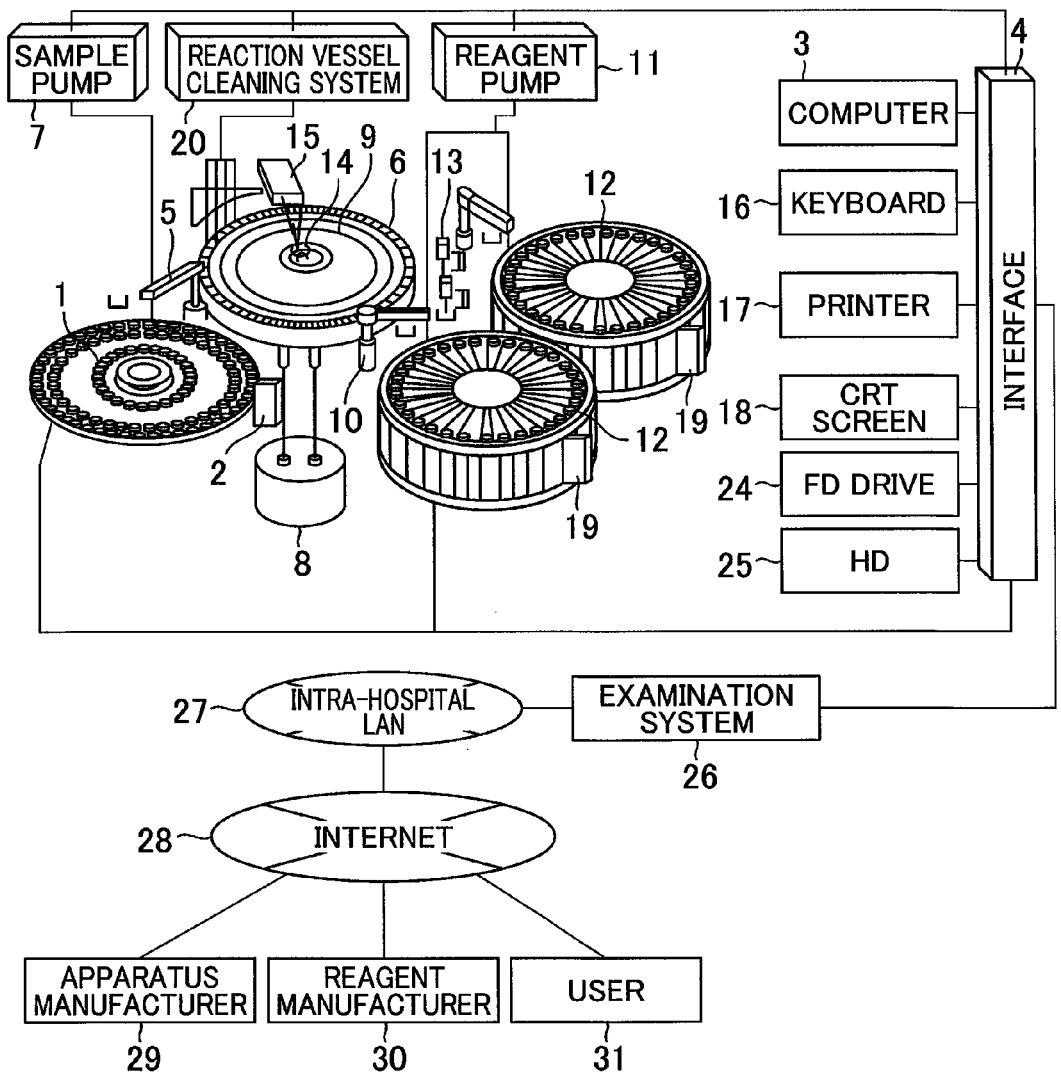
FIG. 1 is a diagram illustrating the input of operation event information.

The present invention relates to a quality control system for a clinical examination automatic analyzer that mainly uses blood, urine, or other patient specimen for clinical examination. More particularly, the present invention relates to a quality control system that extracts the pattern and range of variation in the results of quality control substance measurement and calibration from the result of quality control or calibration that is performed in a laboratory for a predetermined period of time, issues a warning to indicate optimum calibration intervals, and issues a precautionary note to indicate the necessity for additional calibration in accordance with the result of variation in a reagent that is derived from the same lot and used in the other laboratories.

Quality control according to the present invention is, for example, the quality control of biochemical analysis and immunoassay. A quality control chart according to the present invention is, for example, an X bar-Rs-R control chart, an X bar-R control chart, or a twin plot control chart. A calibration result display chart according to the present invention is a graph indicating S1 Abs-S6 Abs, K factor, reagent blank solution main wavelength absorbance, standard solution main wavelength absorbance, and difference between two measurements of standard solution absorbance. A display period is typically one week, which is a period during an operation is usually repeated in a laboratory by default, but not limited to one week.

A vial number according to the present invention is a number identifying a glass or plastic vessel that contains a quality control substance or calibrator derived from the same production lot. A reagent bottle number is a number identifying a bottle that is individually filled with a reagent derived from the same production lot.

A variation pattern according to the present invention is: a stable tendency unaffected by a sample change or by a reagent change; a quality control result shift tendency affected by a control lot change; a shift or drift tendency affected by a control vial change; a calibration result shift or calibration result drift tendency affected by a calibrator lot change; a calibration result shift or calibration result drift tendency affected by a calibrator vial change; a quality control result shift or quality control result drift tendency affected a reagent lot change or by a reagent bottle change; or calibration result shift or calibration result drift tendency affected by a reagent lot change or by a reagent bottle change.

A variation range according to the present invention is a standard deviation among a plurality of quality control or calibration results obtained over a predetermined period or the difference between the maximum and minimum values of these measurement results.

A calibration according to the present invention is a blank calibration, a span calibration, a two-point calibration, or a multi-point calibration. The blank calibration is a calibration technique that merely updates a reagent blank absorbance by using water, saline, or other blank solution. The span calibration is a calibration technique that merely updates a K value by using one standard solution having a known concentration other than a blank solution. The two-point calibration is a calibration technique that updates a calibration curve by measuring a blank solution and one of a plurality of standard solutions. The multi-point calibration is a calibration technique that updates the calibration curve by using all of designated standard solutions.

More specifically, the calculation formula for the K value (K factor) is $K=(S2-S1)/(S2\ Abs-S1\ Abs)$. S2 and S1 are the concentration values of two calibrators, respectively. S2 Abs and S1 Abs are absorbance values derived from calibrations performed with the two calibrators, respectively. A reagent blank solution absorbance is an absorbance value that is derived from a calibrator containing no measurement target, that is, derived from a calibration performed, for instance, with water or saline.

The present invention will now be described in detail with reference to several embodiments.

First Embodiment

First of all, input tools for operation event information will be described with reference to FIG. 1. A barcode on a disc-type sample cup 1 is read by a sample barcode reader 2 to acquire information about the lot number and vial number of a quality control substance or the lot number and vial number of a calibrator. The acquired information is then recorded in a quality control system for biochemical analysis. A barcode on a reagent bottle 12 is read by a reagent barcode reader 19 to acquire the lot number and bottle number of a reagent. The acquired numbers are then recorded in an automatic analysis quality control system. Maintenance information is acquired from a maintenance log of an automatic analyzer. Alarm information is acquired from the automatic analyzer. The acquired information is then recorded in the automatic analysis quality control system.

Alternatively, various items of information may be obtained from the automatic analyzer through an intra-hospital LAN 27 connected to an examination system 26 and through the Internet 28 and shared by an apparatus manufacturer 29, a reagent manufacturer 30, and a user 31. The apparatus manufacturer 29 and the reagent manufacturer 30 provide prompt service or support in accordance with the information shared between them and the user 31. Alternatively, the user 31 may use the Internet 28 to view and manage system information such as quality control and calibration results obtained in a laboratory, even from a distance.

Figure 2:
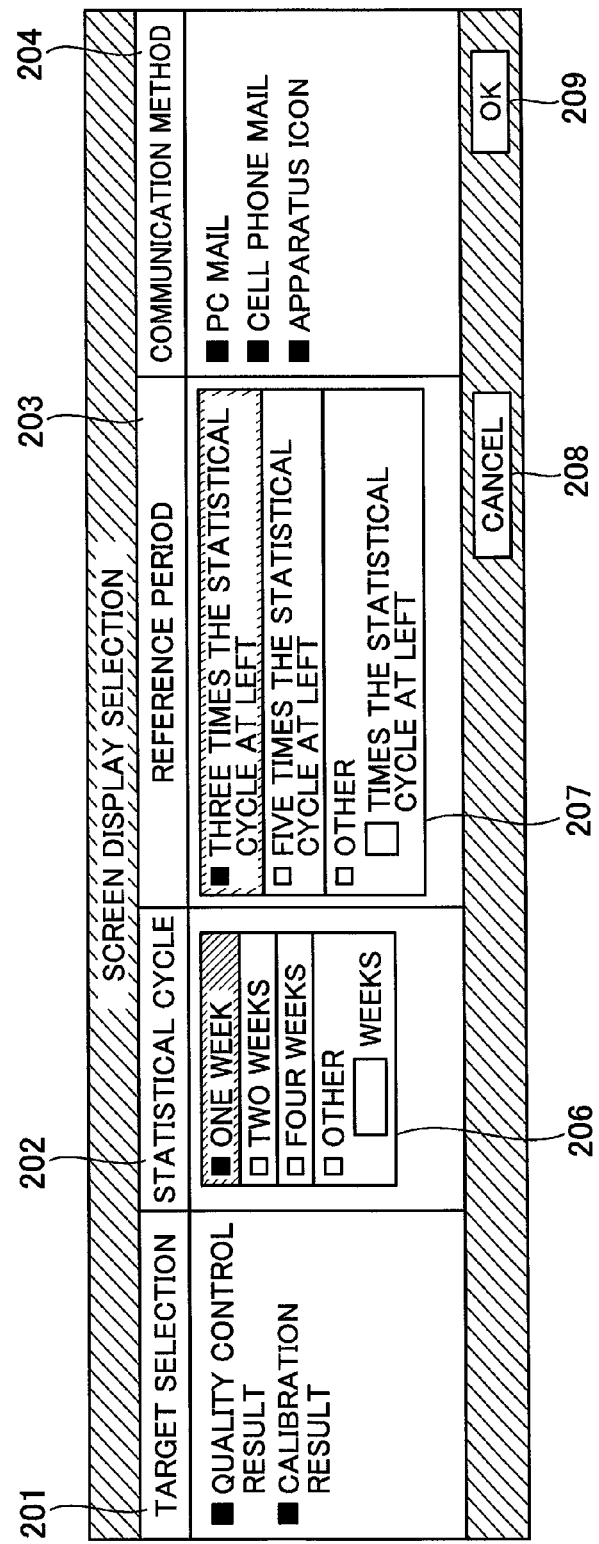
FIG. 2 shows a screen display selection screen.

FIG. 2 shows a typical screen that is used to select information to be displayed on screen. When an OK button 209 is clicked after choosing either QUALITY CONTROL RESULT or CALIBRATION RESULT as a target from SCREEN NAME 201, and selecting a desired STATISTICAL CYCLE 202, a desired REFERENCE PERIOD 203, and a desired COMMUNICATION METHOD 204, the newly input values are stored. If a CANCEL button 208 is clicked, on the other hand, the newly input values are cleared so that the previously input values remain in effect.

If, for instance, "ONE WEEK" is chosen from an input field 206 of STATISTICAL CYCLE 202, the pattern of variation in the quality control or calibration result is calculated and displayed at intervals of one week. If, for instance, "THREE TIMES THE STATISTICAL CYCLE AT LEFT is chosen from an input field 207 of REFERENCE PERIOD 203, optimum calibration intervals are displayed in accordance with the pattern of variation during the last three weeks. If, for instance, PC MAIL, CELL PHONE MAIL, and APPARATUS ICON are selected from COMMUNICATION METHOD 204, the optimum calibration intervals are distributed by PC mail and by cell phone mail and an icon appears on a quality control screen.

Second Embodiment

Figure 3:
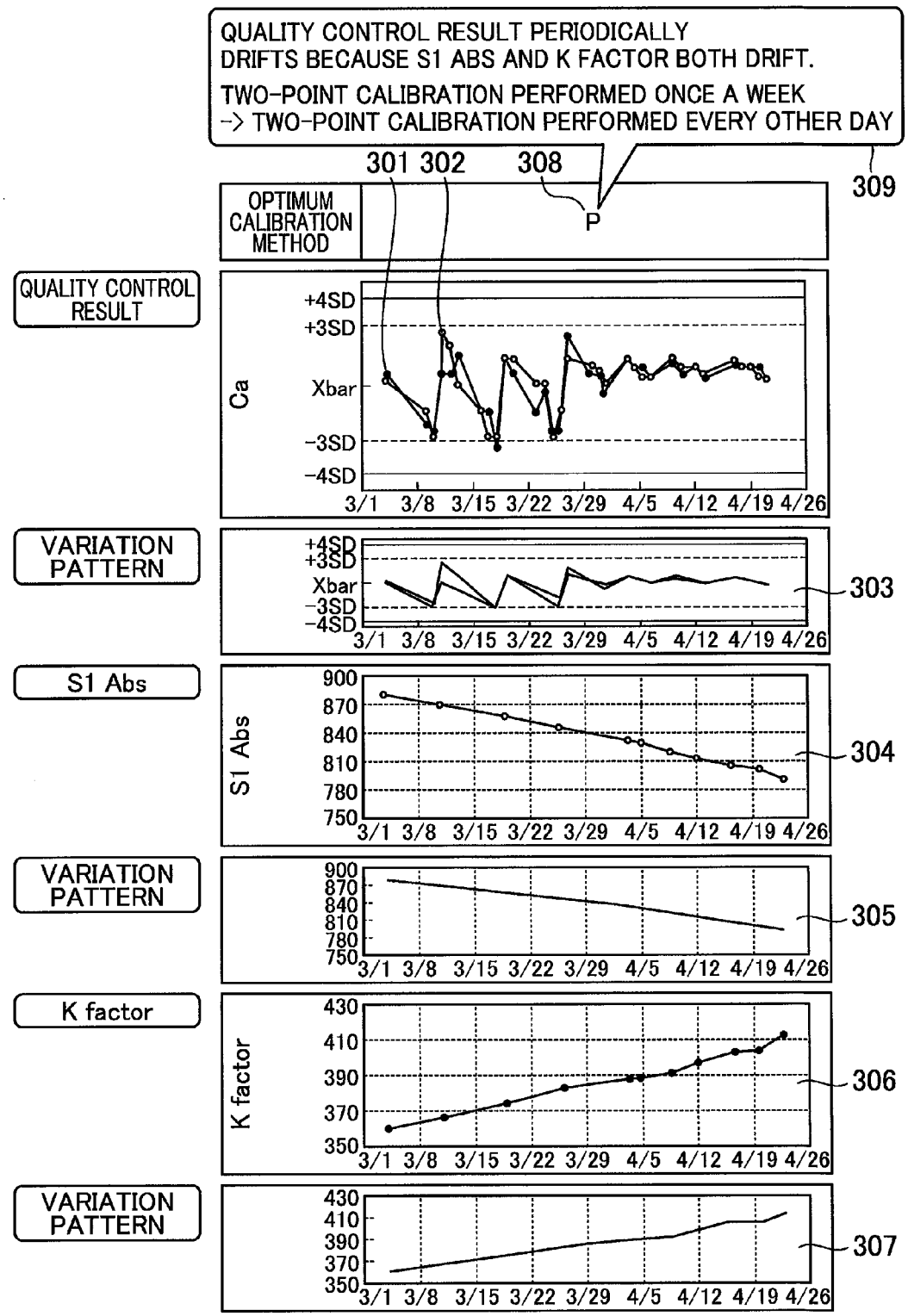
FIG. 3 is a diagram illustrating the results of Ca quality control and calibration.

Referring to FIG. 3, optimum calibration intervals are indicated when the quality control result drifts while S1 Abs and K factor, which are included in the calibration result, drift.

A Ca quality control chart simultaneously displays the measurement result 301 of a low-concentration region quality control substance and the measurement result 302 of a high-concentration region quality control substance. A calculated pattern of variation 303 in the measurement result of a quality control substance is displayed at a statistical cycle of one week. Control charts of S1 Abs 304 and K factor 306, which are included in the calibration result, are displayed. A pattern of variation 305 in the S1 Abs and a pattern of variation 307 in the K factor are respectively displayed at a statistical cycle of one week.

A drift tendency is encountered at intervals of one week in the patterns of variations 305, 307 in the S1 Abs and K factor as well as in the pattern of variation in the measurement result of the quality control substance. However, the calibration performed at intervals of one week is limited to a two-point calibration performed once a week. Therefore, the currently employed calibration method and calibration intervals do not adequately compensate for reagent deterioration. Consequently, a similar weekly drift pattern can be found in the measurement result of the quality control substance.

The same holds true for the pattern of variation during the last three weeks, which is a reference period. Therefore, when an icon 308 indicating an optimum calibration method is clicked, optimum calibration intervals and calibration method 309 are displayed. The aforementioned one-week intervals and displayed icon are merely examples. The present invention is not limited to the use of such an expression method.

For example, when optimum calibration intervals are employed on and after April 1, the reagent is calibrated in detail as far as a two-point calibration is performed every other day. Consequently, no periodic drift is found in the pattern of variation 303 in the result of quality control on and after April 1 although the patterns of variations in the S1 Abs and K factor remain unchanged.

Third Embodiment

Figure 4:
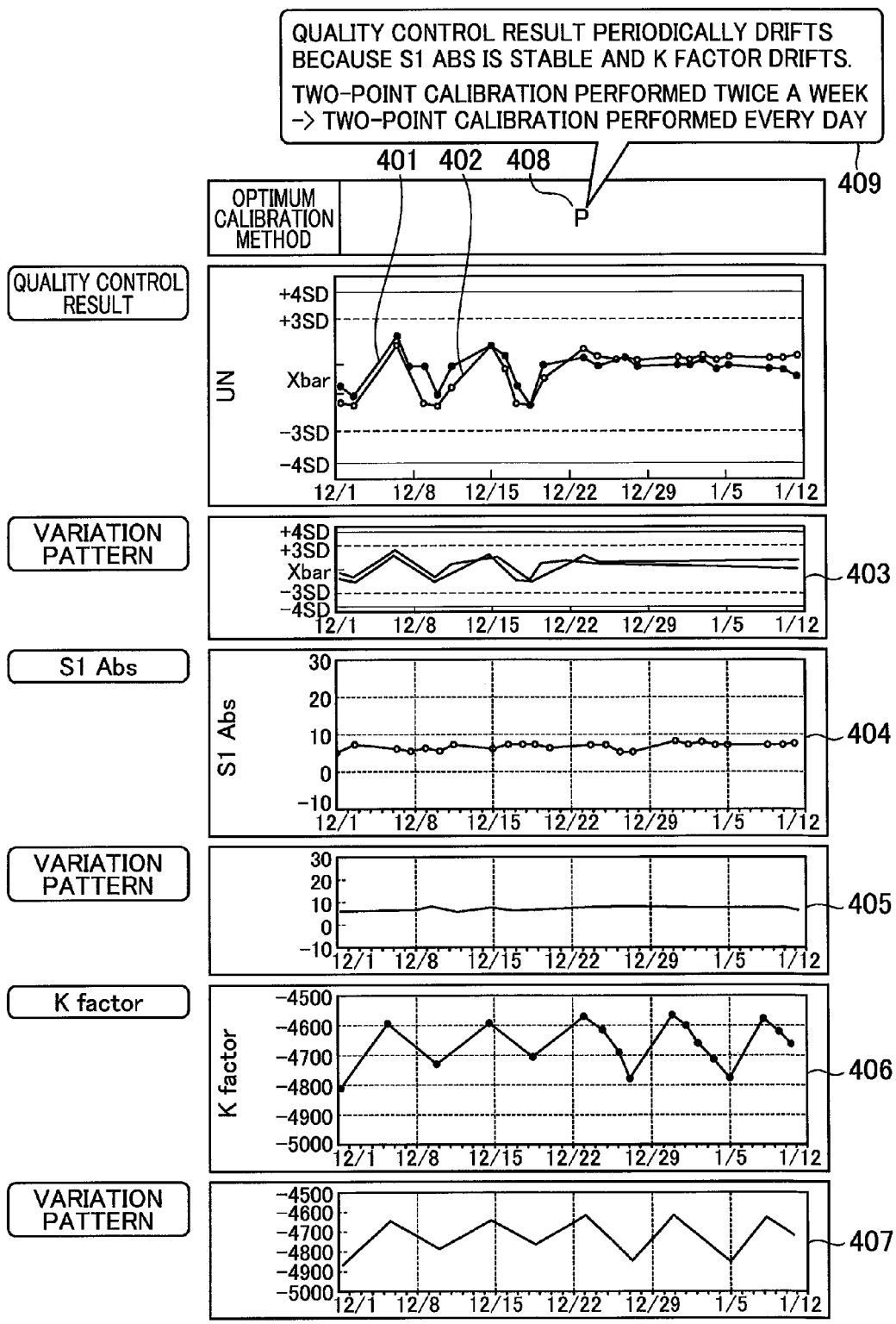
FIG. 4 is a diagram illustrating the results of UN quality control and calibration.

Referring to FIG. 4, optimum calibration intervals are indicated in a situation where the K factor and quality control result both drift although the S1 Abs, which is included in the calibration result, remains stable.

A UN quality control chart simultaneously displays the measurement result 401 of a low-concentration region quality control substance and the measurement result 402 of a high-concentration region quality control substance. A calculated pattern of variation 403 in the measurement result of a quality control substance is displayed at a statistical cycle of one week. Control charts of S1 Abs 404 and K factor 406, which are included in the calibration result, are displayed. A pattern of variation 405 in the S1 Abs and a pattern of variation 407 in the K factor are respectively displayed at a statistical cycle of one week.

A drift tendency is encountered at intervals of one week in the pattern of variation 403 in the measurement result of the quality control substance as well as in the pattern of variation 407 in the K factor although the pattern of variation 405 in the S1 Abs in the calibration measurement result is stable. However, the calibration performed at intervals of one week is a two-point calibration for the beginning of a week and three days later and a blank calibration for the remaining days. Therefore, the intervals at which the two-point calibration is performed are unduly long although the K factor varies. Hence, reagent deterioration is not adequately compensated for. Consequently, a similar weekly drift pattern can be found in the measurement result of the quality control substance.

The same holds true for the pattern of variation during the last three weeks, which is a reference period. Therefore, when an icon 408 indicating an optimum calibration method is clicked, optimum calibration intervals and calibration method 409 are displayed. The aforementioned one-week intervals and displayed icon are merely examples. The present invention is not limited to the use of such an expression method.

For example, when optimum calibration intervals are employed on and after December 23, the reagent is adequately calibrated as far as a two-point calibration is performed every day. Consequently, no periodic drift is found in the pattern of variation 403 in the result of quality control on and after December 23 although the pattern of variation in the K factor remains unchanged.

Fourth Embodiment

Figure 5:
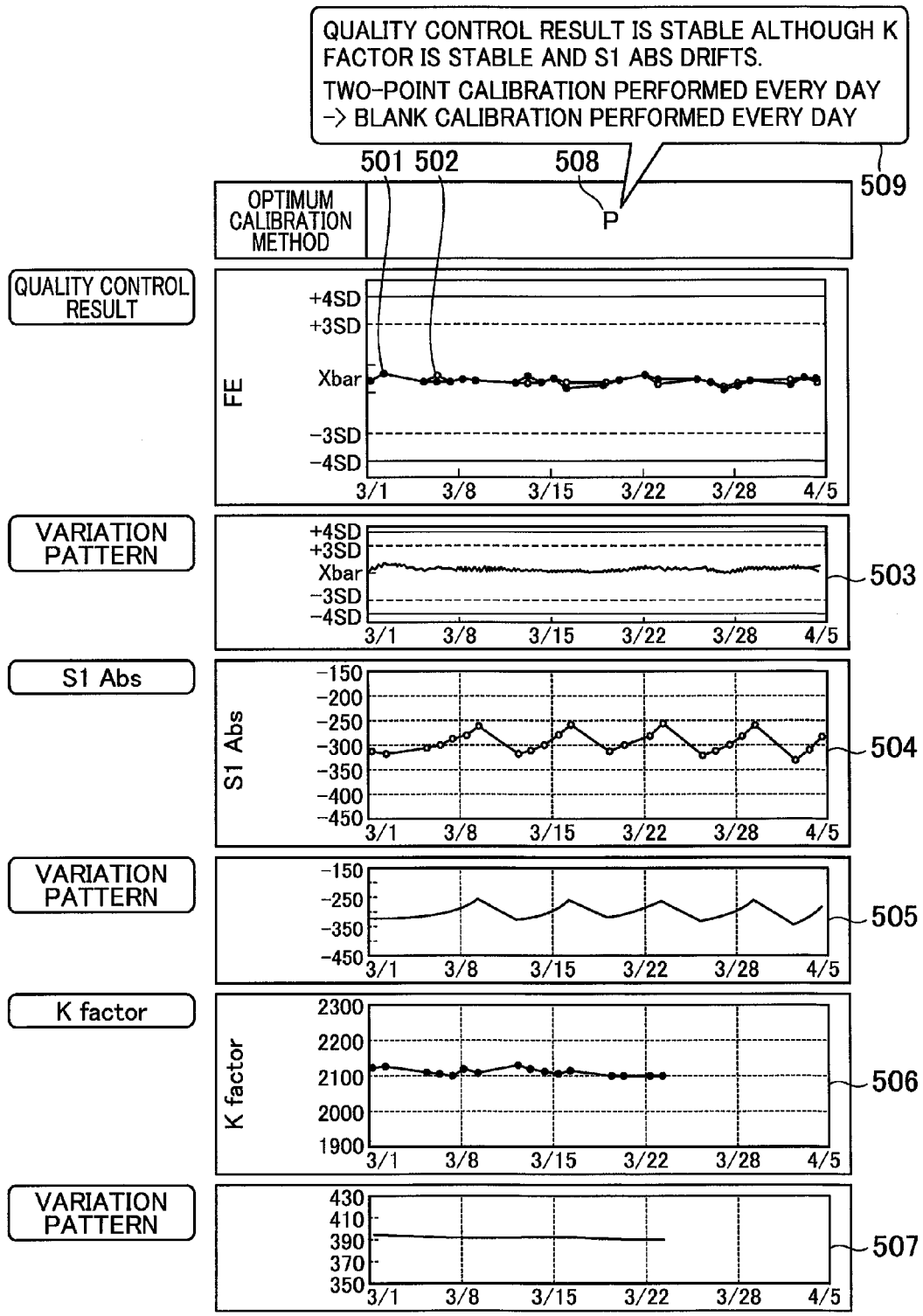
FIG. 5 is a diagram illustrating the results of FE quality control and calibration.

Referring to FIG. 5, optimum calibration intervals are indicated in a situation where the S1 Abs and quality control result both drift although the K factor, which is included in the calibration result, remains stable.

An FE quality control chart simultaneously displays the measurement result 501 of a low-concentration region quality control substance and the measurement result 502 of a high-concentration region quality control substance. A calculated pattern of variation 503 in the measurement result of a quality control substance is displayed at a statistical cycle of one week. Control charts of S1 Abs 504 and K factor 506, which are included in the calibration result, are displayed. A pattern of variation 505 in the S1 Abs and a pattern of variation 507 in the K factor are respectively displayed at a statistical cycle of one week.

A drift tendency is encountered at intervals of one week in the pattern of variation 505 in the S1 Abs, which is included in the calibration result, although the pattern of variation 503 in the measurement result of the quality control substance and the K factor 506 included in the calibration measurement result are stable. The calibration performed at intervals of one week is a two-point calibration performed every day. Hence, reagent deterioration is adequately compensated for. Consequently, the measurement result of the quality control substance is found to be stable.

The same holds true for the pattern of variation during the last three weeks, which is a reference period. Therefore, when an icon 508 indicating an optimum calibration method is clicked, optimum calibration intervals and calibration method 509 are displayed. The aforementioned one-week intervals and displayed icon are merely examples. The present invention is not limited to the use of such an expression method.

For example, when optimum calibration intervals are employed on and after March 23, the reagent is adequately calibrated even if a blank calibration is performed every day instead of performing a two-point calibration every day. Consequently, the pattern of variation 503 in the quality control result obtained on and after March 23 is found to be still stable although the pattern of variation in the S1 Abs remains unchanged.

Fifth Embodiment

Figure 6:
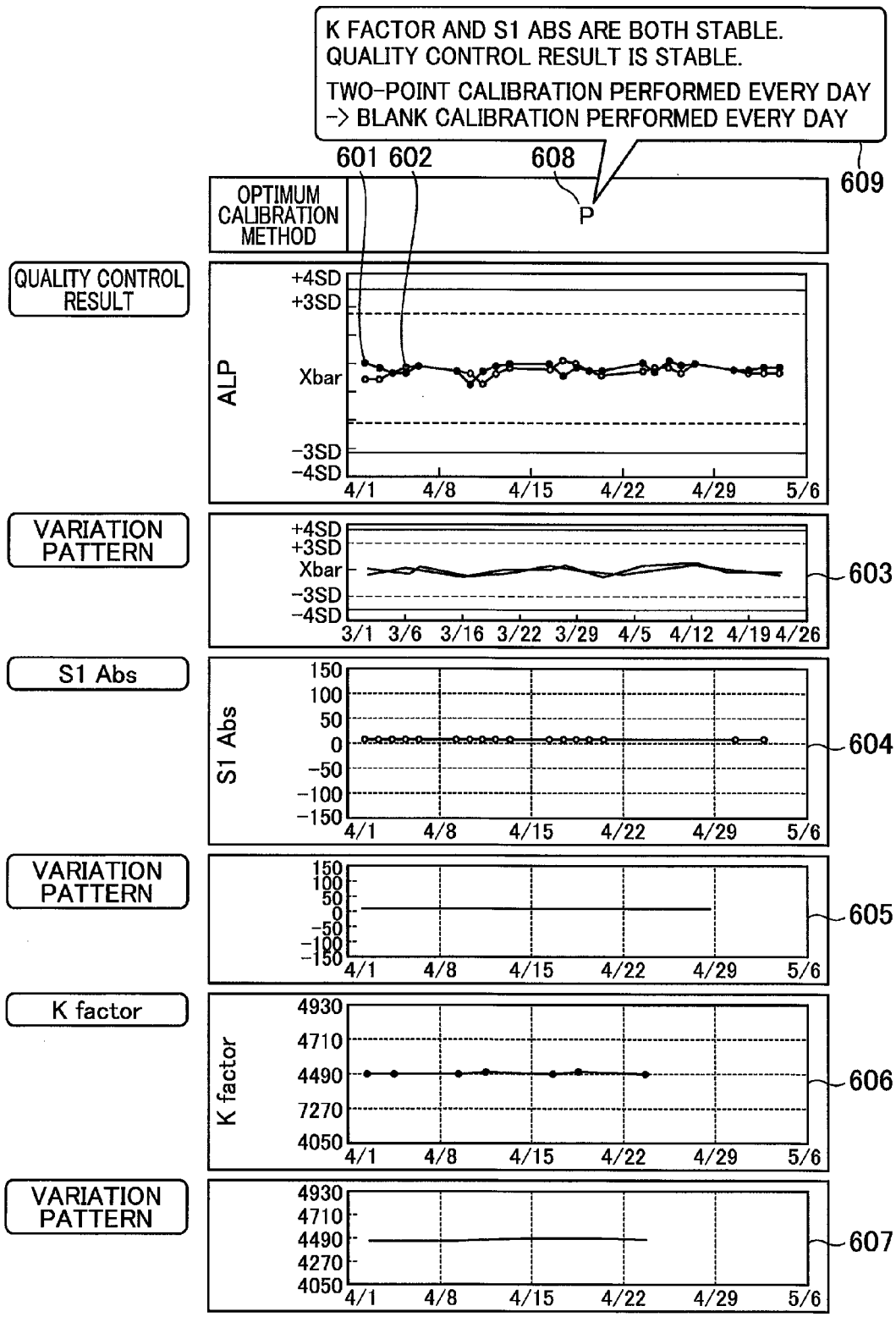
FIG. 6 is a diagram illustrating the results of ALP quality control and calibration.

Referring to FIG. 6, optimum calibration intervals are indicated in a situation where the quality control result and the S1 Abs and K factor, which are included in the calibration result, are both stable.

An ALP control chart simultaneously displays the measurement result 601 of a low-concentration region quality control substance and the measurement result 602 of a high-concentration region quality control substance. A calculated pattern of variation 603 in the measurement result of a quality control substance is displayed at a statistical cycle of one week. Control charts of S1 Abs 604 and K factor 606, which are included in the calibration result, are displayed. A pattern of variation 605 in the S1 Abs and a pattern of variation 607 in the K factor are respectively displayed at a statistical cycle of one week.

The pattern of variation 603 in the measurement result of the quality control substance and the S1 Abs 604 and K factor 606, which are included in the calibration measurement result, are stable. The calibration performed at intervals of one week is a two-point calibration for the beginning of a week and two days later and a blank calibration for the remaining days. Hence, reagent deterioration is adequately compensated for. Therefore, the measurement result of the quality control substance is found to be stable. When a conventional reagent is used, calibration is performed at short intervals because it is anticipated that an unsealed ALP reagent may deteriorate. However, the stability of a reagent is increased due to reagent improvement. Consequently, the calibration measurement result is also found to be stable.

The same holds true for the pattern of variation during the last three weeks, which is a reference period. Therefore, when an icon 608 indicating an optimum calibration method is clicked, optimum calibration intervals and calibration method 609 are displayed. The aforementioned one-week intervals and displayed icon are merely examples. The present invention is not limited to the use of such an expression method.

For example, when optimum calibration intervals are employed on and after April 23, the reagent is adequately calibrated even if a blank calibration is performed every other day instead of performing a two-point calibration twice a week. Consequently, the pattern of variation 603 in the quality control result obtained on and after April 23 is found to be still stable although the pattern of variation in the S1 Abs remains unchanged.

DESCRIPTION OF REFERENCE NUMERALS

1 . . . Sample cup
2 . . . Sample barcode reader
3 . . . Computer
4 . . . Interface
5 . . . Sample dispensing probe
6 . . . Reaction vessel
7 . . . Sample pump
8 . . . Thermostatic bath
9 . . . Reaction compartment
10 . . . Reagent dispensing probe
11 . . . Reagent pump
12 . . . Reagent bottle
13 . . . Agitator
14 . . . Light source
15 . . . Multi-wavelength photometer
16 . . . Keyboard
17 . . . Printer
18 . . . CRT screen
19 . . . Reagent barcode reader
20 . . . Reaction vessel cleaning system
24 . . . FD drive
25 . . . HD
26 . . . Examination system 27 ... Intra-hospital LAN
28 ... Internet
29 ... Apparatus manufacturer
30 ... Reagent manufacturer
31 ... User

The invention claimed is:

1. An automatic analyzer, comprising:
a sample cup having a barcode attached thereto and holding a quality control substance;
a sample barcode reader configured to read the barcode attached to the sample cup;
a multi-wavelength photometer configured to measure a solution containing the quality control substance;
a display; and
a control unit connected to the sample barcode reader, the multi-wavelength photometer, and the display,
wherein the control unit is programmed to:
identify a lot number and vial number of the quality control substance based on information read by the barcode reader,
display a measurement result in a low-concentration region of the quality control substance on the display,
display a measurement result in a high-concentration region of the quality control substance on the display,
calculate a variation pattern of at least one of the measurement in the low-concentration region and the high-concentration region of the quality control substance and display the variation pattern on the display,
store the calculated variation patterns based on a time of calculation,
display a selection screen on the display enabling selection of a time period to display the measurement result in the low-concentration region, the measurement result in the low-concentration region, and the variation pattern, and enabling selection of a time frame from which the calculation of the variation pattern is calculated,
calculate an optimum calibration interval and method based on the stored calculated variation patterns
display the calculated optimum calibration interval and method on the display screen.

2. The automatic analyzer of claim 1,
wherein, the control unit is further programmed to determine whether the stored variation patterns periodically drift together with an S1 Abs and a K factor, and if the stored variation patterns drift, a two-point calibration is determined to be optimum calibration method at shortened intervals.

3. The automatic analyzer of claim 1,
wherein the display of the measurement result in the low-concentration region of the quality control substance, the display a measurement result in the high-concentration region of the quality control substance and the variation pattern are displayed simultaneously during the time period.

* * * * *